United States Patent [19]

Taylor

[11] Patent Number: 4,961,982
[45] Date of Patent: Oct. 9, 1990

[54] LIQUID-ABSORBING PAD ASSEMBLY AND METHOD OF MAKING SAME

[75] Inventor: Jeffrey L. Taylor, Cincinnati, Ohio

[73] Assignee: Standard Textile Company, Inc., Cincinnati, Ohio

[21] Appl. No.: 323,765

[22] Filed: Mar. 15, 1989

Related U.S. Application Data

[63] Continuation of Ser. No. 253,667, Oct. 5, 1988, abandoned, which is a continuation of Ser. No. 139,185, Dec. 29, 1987, abandoned, which is a continuation of Ser. No. 911,974, Sep. 25, 1986, abandoned.

[51] Int. Cl.⁵ .............................................. B32B 33/00
[52] U.S. Cl. ................................... 428/41; 5/484; 5/502; 112/265.1; 156/60; 156/93; 156/290; 156/367.8; 428/102; 428/142; 428/143; 428/246; 428/253; 428/224; 428/287; 428/364.4; 428/316.6; 428/492; 428/913; 604/369
[58] Field of Search ............... 604/369; 156/60, 93, 156/290, 307.3; 428/102, 91, 246, 253, 284, 287, 492, 913, 304.4, 316.6, 192, 193; 112/265.1; 5/484, 502

[56] References Cited

U.S. PATENT DOCUMENTS

| | | | |
|---|---|---|---|
| 30,972 | 6/1982 | Hyle et al. | 428/219 |
| 2,682,873 | 7/1954 | Evans et al. | 128/156 |
| 2,893,105 | 7/1959 | Lauterbach | 28/72.2 |
| 2,910,763 | 11/1959 | Lauterbach | 28/72.2 |
| 3,065,751 | 11/1962 | Gobbo | 128/287 |
| 3,468,311 | 9/1969 | Gallagher | 604/370 |
| 3,691,570 | 9/1972 | Gaines et al. | 428/296 |
| 3,709,221 | 1/1973 | Riely | 128/156 |
| 3,721,242 | 3/1973 | Krusko | 128/284 |
| 3,763,863 | 10/1973 | Mesek et al. | 128/284 |
| 3,768,480 | 10/1973 | Mesek et al. | 128/284 |
| 3,801,420 | 4/1974 | Anderson | 161/52 |
| 3,812,001 | 5/1974 | Ryan | 161/114 |
| 3,840,013 | 10/1974 | Mesek et al. | 604/370 |
| 3,863,637 | 2/1975 | MacDonald et al. | 604/370 |
| 3,871,037 | 3/1975 | Willington | 5/91 |
| 3,888,257 | 6/1975 | Cook et al. | 128/296 |
| 3,916,900 | 11/1975 | Breyer et al. | 604/369 |
| 3,921,639 | 11/1975 | Cepuritis | 604/377 |
| 3,965,906 | 6/1976 | Harami | 128/287 |
| 3,967,623 | 7/1976 | Butterworth et al. | 128/156 |
| 3,989,867 | 11/1976 | Sisson | 428/132 |
| 3,993,828 | 11/1976 | McCorsley | 428/236 |
| 4,029,100 | 6/1977 | Karami | 128/284 |
| 4,042,986 | 8/1977 | Goodman | 5/335 |
| 4,051,848 | 10/1977 | Levine | 128/156 |
| 4,057,669 | 11/1977 | McConnell | 428/152 |
| 4,077,410 | 3/1978 | Butterworth et al. | 128/287 |
| 4,097,943 | 7/1978 | O'Connell | 5/335 |
| 4,125,114 | 11/1978 | Repke | 128/280 |
| 4,195,634 | 4/1980 | DiSalvo et al. | 128/290 R |
| 4,210,144 | 7/1980 | Sarge et al. | 128/287 |
| 4,216,774 | 8/1980 | Graber | 604/371 |
| 4,360,021 | 11/1982 | Stema | 428/68 |

*Primary Examiner*—James J. Bell
*Attorney, Agent, or Firm*—Kinney & Schenk

[57] ABSTRACT

A liquid-absorbing pad assembly and method of making same are provided wherein such assembly comprises a top layer, a bottom waterproof layer, an absorbent layer between the top and bottom layers, and a multiple-purpose structure disposed between the absorbent layer and the top layer, such structure providing cushioning, means enabling immediate passage therethrough of liquid from the top layer, means substantially preventing reverse wicking of liquid that has passed through the structure, and a suspension which allows air to freely associate with the underside of said top layer for drying purposes.

34 Claims, 3 Drawing Sheets

LIQUID-ABSORBING PAD ASSEMBLY AND METHOD OF MAKING SAME

This is a Continuation, of application Ser. No. 253,667 filed Oct. 5, 1988 abandoned.

BACKGROUND OF THE INVENTION

1. Field of the Invention

This invention relates to a liquid-absorbing pad assembly and to a method of making such pad assembly and in particular to a pad assembly which may be used on a bed, chair, wheel chair, or the like; and, such pad assembly has particular use in keeping a urinary incontinent patient, a surgical patient, or anyone subject to drainage of body fluid(s) for example, dry and comfortable.

2. Prior Art Statement

It is known in the art to provide a liquid-absorbing pad assembly which comprises a top layer, a bottom waterproof layer, and an absorbent layer disposed therebetween; and, such a liquid-absorbing pad assembly has been proposed for use as a bed pad and as a chair pad.

SUMMARY OF THE INVENTION

One feature of this invention is to provide a new liquid-absorbing pad assembly comprising a top layer, a bottom waterproof layer, and an absorbent layer disposed therebetween. The new liquid-absorbing pad assembly of this invention is particularly adapted to be used with a patient having urinary incontinence. The pad assembly is also effective in absorbing other liquids as well as blood, in the case of the surgical patient; and, the pad assembly serves to keep liquids away from a person's body so as to assure optimum comfort and the prevention of bed sores, and the like.

In accordance with one embodiment Of the new liquidabsorbing pad assembly of this invention a multiple-purpose structure is dispOsed between the absorbent layer and the top layer with the structure providing cushioning, means enabling immediate passage therethrough of liquid from the top layer, means substantially preventing reverse wicking of liquid that has passed through the structure, and a suspension which allows air to freely associate with the underside of the top layer for drying purposes.

Accordingly, it is an object of this invention to provide a new liquid-absorbing pad assembly having one or more of the novel features of this invention as set forth above or hereinafter shown or described.

Another object of this invention is to provide a new method of making such a liquid-absorbing pad assembly with the method of this invention having one or more of the novel features of this invention as set forth above or hereinafter shown or described.

Other features, objects, uses, and advantages of this invention are apparent from a reading of this description which proceeds with reference to the accompanying drawings forming a part thereof.

BRIEF DESCRIPTION OF THE DRAWINGS

The accompanying drawings show present preferred embodiments of this invention, in which.

DESCRIPTION OF THE PREFERRED EMBODIMENTS

Figure 1:
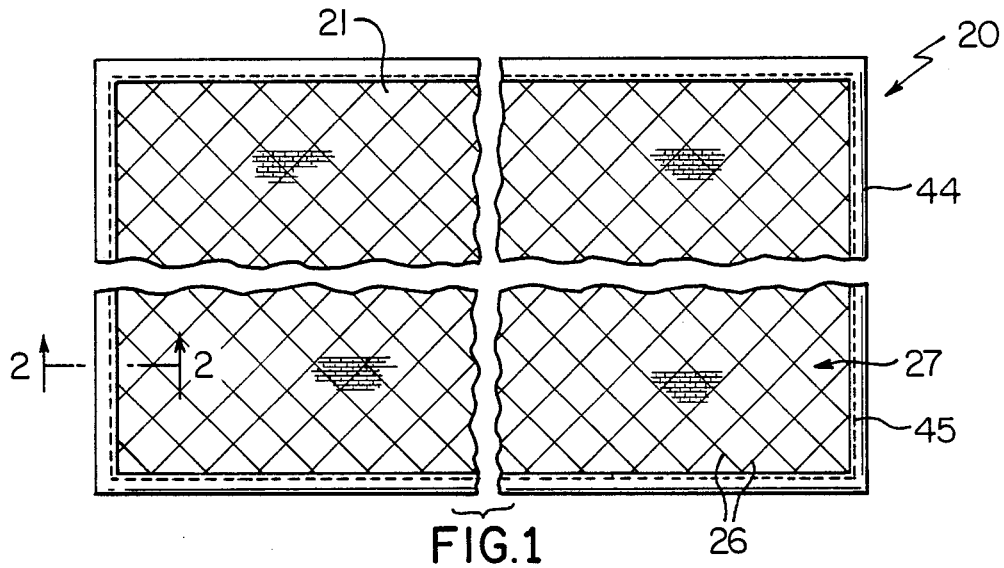
FIG. 1 is a plan view of one exemplary embodiment of the liquid-absorbing pad assembly of this invention with the central portion thereof broken away.

While the various features of this invention are hereinafter illustrated and described as being particularly adapted to provide a liquid-absorbing pad assembly usable as a bed pad, chair pad, wheel chair pad, and the like, in a manner known in the art, it is to be understood that the various features of this invention can be utilized singly or in various combinations thereof to provide a liquid-absorbing pad assembly usable with other liquids and in other applications, as desired.

Therefore, this invention is not to be limited to only the embodiments illustrated in the drawings, because the drawings are merely utilized to illustrate exemplary ones of the wide variety of uses of this invention.

Reference is now made to FIG. 1 of the drawings which illustrates one exemplary embodiment of the liquid-absorbing pad assembly of this invention which is designated generally by the reference numeral 20. The pad assembly 20 is particularly adapted to be used as a bed pad, chair pad, wheel chair pad, or the like; and, such pad assembly is particularly adapted for use with a patient having urinary incontinence, or anyone subject to drainage of body fluids.

Figure 2:
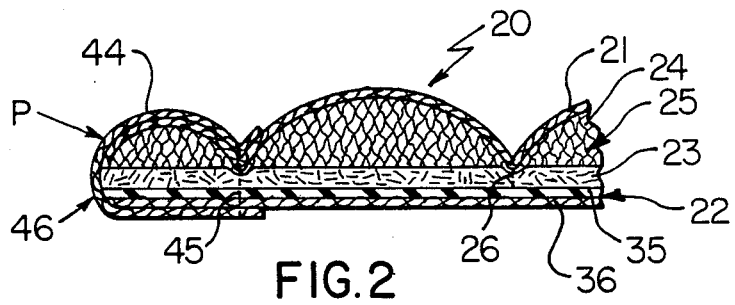
FIG. 2 is an enlarged, cross-sectional view taken essentially on the line 2—2 of FIG. 1.

As seen in FIG. 2, the pad assembly 20 has a peripheral outline P and comprises a top layer 21, a bottom water-proof layer which is designated generally by the reference numeral 22, and an absorbent layer 23 between the top and bottom layers. In accordance with the teachings of this invention the pad assembly 20 comprises a multiple-purpose structure 24 disposed between the absorbent layer 23 and the top layer 21 and the structure 24 provides or serves the multiple-purpose of cushioning, provides means enabling immediate passage therethrough of liquid from the top layer, provides means substantially preventing reverse wicking back toward the top layer 21 of liquid that has passed downwardly through the structure 24, and provides a suspension which allows air to freely associate with the underside of the said top layer 21 for drying purposes.

Figure 11:
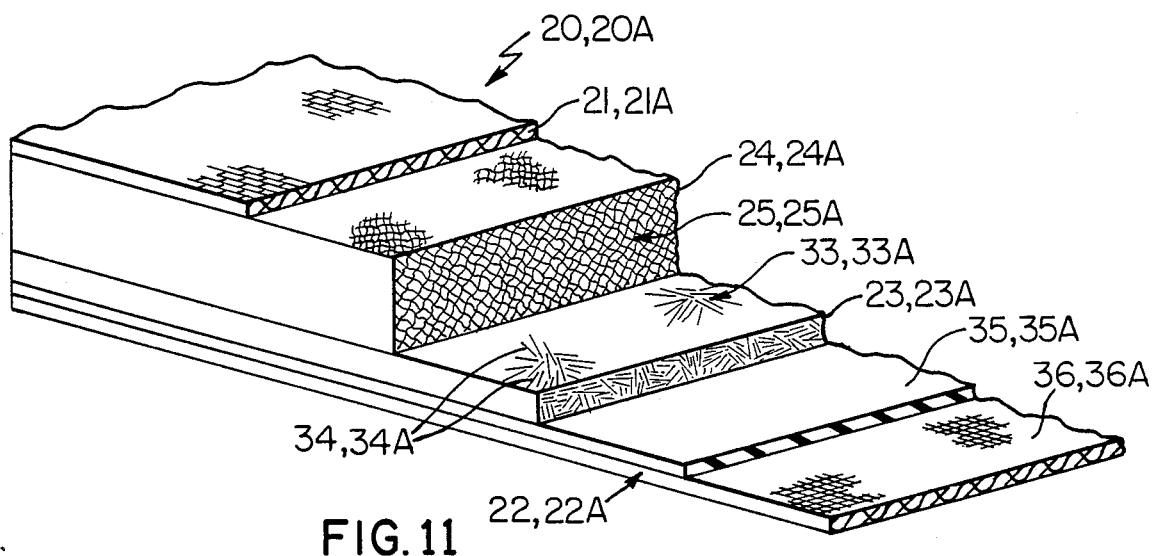
FIG. 11 is a fragmentary isometric view presented to show the overall stacked arrangement of the various layers of each pad assembly minus the details applicable to either of the two illustrated embodiments.

The structure 24 is a resilient sheet of a foamed synthetic plastic material having a reticulated construction; and, such reticulated construction and foamed character thereof are illustrated typically at 25 in FIGS. 2 and 11.

The pad assembly 20 has its top layer 21, structure 24, and absorbent layer 23 held together by stitch means 26 disposed inwardly of its peripheral outline P; and such stitch means define a quilted construction. The stitch means or stitches 26 pull the top layer 21, structure 24, and absorbent layer together in a plurality of locations, shown typically at 27 in FIGS. 1 and 3, defining a patterned outline which is illustrated, in this example, as a roughly rectangular outline when viewed normal to the top layer 21.

Each patterned outline 27 has a central part (FIG. 4) and the resilient sheet has a predetermined thickness 28 which when measured at each central part comprises a major portion of the overall thickness 29 of the pad assembly 20.

Figure 3:
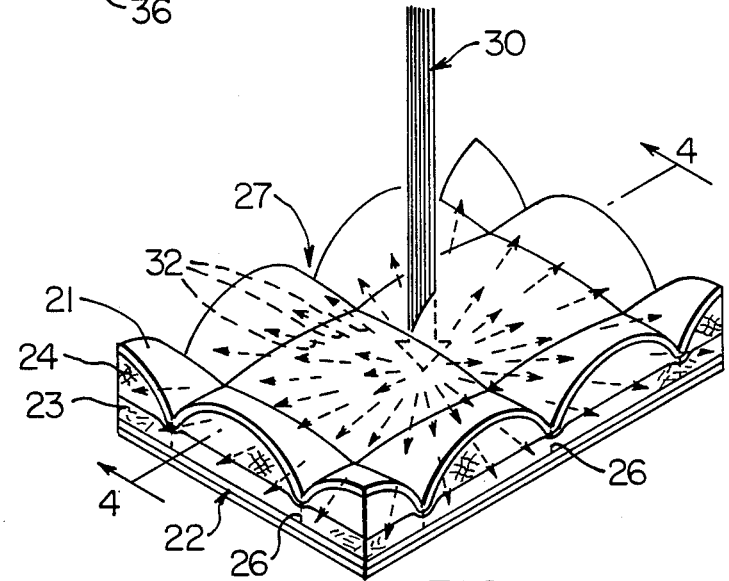
FIG. 3 is a schematic isometric view illustrating the manner in which an absorbent layer of the pad assembly serves to dissipate liquid radially from a local introduction point throughout a substantial volume of the absorbent layer.
Figure 4:
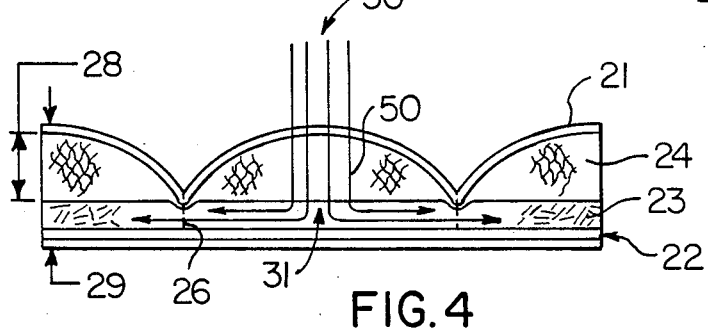
FIG. 4 is a schematic view taken essentially on the line 4—4 of FIG. 3.
Figure 5:
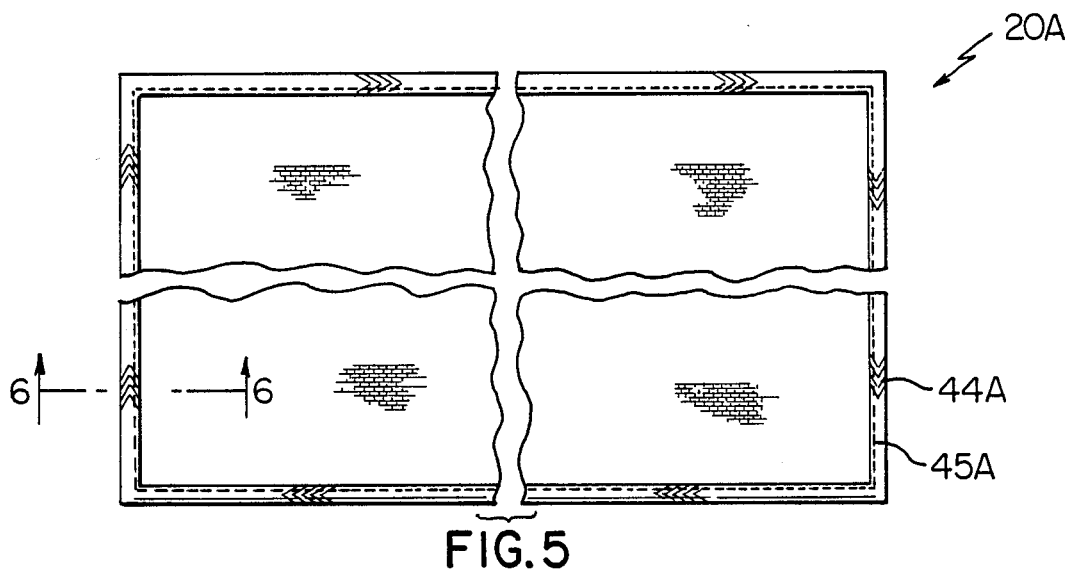
FIG. 5 is a plan view similar to FIG. 1 of another exemplary embodiment of the liquid-absorbing pad assembly of this invention with the central portion thereof broken away.

It will also be seen particularly in FIGS. 2-4 of the drawings that the stitches 26 do not extend through and hence do not puncture the bottom layer 22 whereby the liquid impervious integrity of the pad 20 is assured.

The structure 24 of pad assembly 20 is the type of structure that does not store any liquid, such as urine. Indeed, it is the type of structure that allows substantially immediate passage of any liquid therethrough without any tendency to absorb such liquid.

The structure 24 may be made by any suitable process and is preferably made by a foaming process such that it has cellular walls which define the reticulated construction thereof; and, such structure is a resilient skeletal structure which enables it to provide a cushioning function. Further, due to the openness thereof the structure 24 allows immediate passage therethrough of liquids such as urine, blood, or the like. In addition, the structure 24 is such that it prevents reverse wicking of liquid initially from the top layer that has passed through such structure. However, the structure 24 is sufficiently strong that it serves as a suspension for the top layer 21 especially within the confines of each rectangular outline defined by the stitch means 26. The suspension so defined is so open that it allows air to freely associate with the underside of such top layer, as previously mentioned, whereby in the event the top layer 21 becomes wet with urine, for example, the structure 24 allows air to freely associate and engage the underside of the top layer and provide a drying action. The overall result is that the top layer 21 dries rapidly and with a patient laying on such top layer there is minimum amount of time that the top layer would remain wet and thereby keep the patient's skin wet. Accordingly, with the use of pad 20 there is minimum discomfort to a patient lying thereon and less tendency for the patient to have bed sores, or the like.

The top layer 21 of the pad assembly 20 is preferably in the form of a fabric layer and in particular in the form of a napped tricot. Preferably the napped tricot is a loop napped tricot whereby it has a napped surface texture which is defined by its knitted construction and not defined by any other process by which a napped surface texture might be provided. The napped tricot fabric layer 21 is preferably made entirely of polyester yarns. However, it is to be understood that such layer may be made of other materials and other knitted, woven, or nonwoven constructions, as desired, and as is known in the art.

As previously mentioned the liquid-absorbing pad assembly 20 comprises an absorbent layer 23 and such absorbent layer is preferably in the form of a nonwoven fibrous mat. The fibrous mat serves to dissipate liquid radially from any local introduction point thereon throughout a substantial region or portion of its volume. To highlight this phenomenon particular reference is made to FIGS. 3 and 4 of the drawings in which liquid 30 is shown schematically by the lines 30 and is introduced at an exemplary local introduction point 31. The construction of the fibrous mat 23 is such that such liquid is dissipated radially throughout a substantial volume of the mat 23, as indicated by the radial dotted arrows in FIG. 3 and a representative few of such arrows are designated by the same reference numeral 32.

The absorbent layer or mat 23 is comprised of randomly disposed fibers as shown at 33 in FIG. 11 which are preferably in the form of randomly disposed bonded fibers which are bonded together at various points throughout their lengths and such fibers are designated generally by the reference numeral 34 with a few representative fibers being so designated. The fibers 34 may be in the form of polyester or other suitable fibers.

As indicated previously, the pad assembly 20 comprises a waterproof layer 22 and such waterproof layer is best illustrated in FIGS. 2 and 11 and comprises a polymeric sheet portion 35 and a woven fabric portion 36 which are bonded together free of additional adhesive means therebetween. The polymeric sheet portion 35 is preferably made of any suitable liquid impervious polymeric material and in one exemplary embodiment of this invention the sheet portion 35 was made of a butyl rubber. The woven fabric material 36 of the waterproof layer 22 is a plainwoven fabric comprised of cotton and polyester. The woven fabric serves to protect the polymeric layer against abrasion, provides dimensional stability to the overall waterproof layer 22, and provides a non-skid surface to the bottom of the pad assembly 20. Although various yarns may be utilized to define the warps and wefts of the plainwoven fabric 36, in this exemplary embodiment it is made of 50% cotton and 50% polyester.

The polymeric sheet portion 35 or sheet 35 is preferably capable of withstanding hydrostatic water pressure of 100 pounds per square inch gauge (psig) without allowing passage of water therethrough. However, it will be appreciated that the particular polymeric sheet portion 35 utilized in the pad assembly 20 may be constructed of any desired fluid impervious material and have any desired thickness such that it would be capable of withstanding hydrostatic water pressures of more than 100 psig or less than 100 psig, as desired.

It will also be appreciated that the polymeric sheet 35 and the woven fabric 36 are laminated or bonded together without additional adhesive means therebetween. This is achieved by extruding polymeric sheet directly against the woven fabric 36 after forming the polymeric sheet 35 in suitable calender rolls, or the like, as is known in the art. The polymeric sheet 35 may also be knife-coated onto the woven fabric 36 or applied by any other suitable means known in the art. The thickness of the coating in this latter type of application may be controlled utilizing suitable doctor blades.

The pad assembly 20 preferably has what is commonly referred to as a binding tape 44 which protects the peripheral edges of its layers and defines the peripheral outline P thereof. The binding tape 44 may be any suitable tape known in the art and may be made of any suitable material. Preferably the binding tape 44 is made of 100% polyester and is in the form of a so-called bias tape which is fastened in position by suitable stitch means or stitches 45. The techniques used to define the corners of the pad assembly and the manner of attaching the bias binding tape 44 at such corners is in accordance with standard practice and is well known in the art. In the process of stitching the binding tape 44 in position the pad assembly 20 has a compressed peripheral edge portion defined by an outer portion which has a substantially D-shaped cross-sectional configuration, as shown at 46.

As mentioned earlier stitch means or stitches 26 hold the top layer 21, structure 24, and absorbent layer 23 together and define the quilted construction. The technique used to make the quilted construction may be any suitable technique known in the art. Further, after defining a quilted construction of the desired size and shape the binding tape is sewn in position to complete the pad assembly 20. The pad assembly thus defined does not have, i.e., is free of attaching means or fasteners between the quilted construction and the bottom sheet inwardly of the peripheral stitches 45. It has been found that this construction is satisfactory even through a large number of washings of the assembly 20, as will be described subsequently.

Another exemplary embodiment of the pad assembly of this invention is illustrated in FIGS. 5–10. The pad assembly 20A illustrated in FIGS. 5–10 is very similar to the pad assembly 20. Therefore, such pad assembly will be designated generally by the reference numeral 20A and representative parts thereof which are similar to corresponding parts of the pad assembly 20 will be designated in the drawings by the same reference numeral as in the pad assembly 20 (whether or not such representative parts are mentioned in the specification) followed by the associated letter designation A and not described again in detail. Only those component parts of the pad assembly 20A of FIGS. 5–10 which are substantially different from corresponding parts of the assembly 20 will be designated by a new reference numeral also followed by the associated letter designation and described in detail.

The pad assembly 20A of FIGS. 5–10 comprises a top layer 21A a bottom waterproof layer which is designated generally by the reference numeral 22A and an absorbent layer 23A between the top and bottom layers, The pad assembly 20A also comprises a multiple-purpose structure 24A laminated between the waterproof layer 23A and the top layer 21A and in a similar manner as described in connection with the pad assembly 20, the structure 24A provides or serves the multiple-purpose of cushioning, provides means enabling immediate passage therethrough of liquid from the top layer, provides means preventing reverse wicking back toward the top layer 21A of liquid that has passed downwardly through the structure 24A, and provides a suspension which allows air to freely associate with the underside of the top layer 21A for drying purposes.

Figure 6:
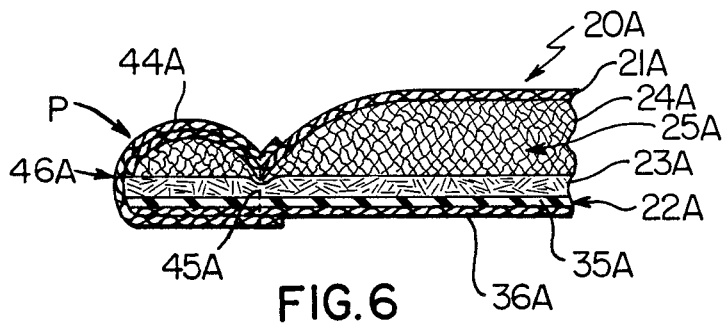
FIG. 6 is an enlarged, cross-sectional view taken essentially on the line 6—6 of FIG. 5.
Figure 8:
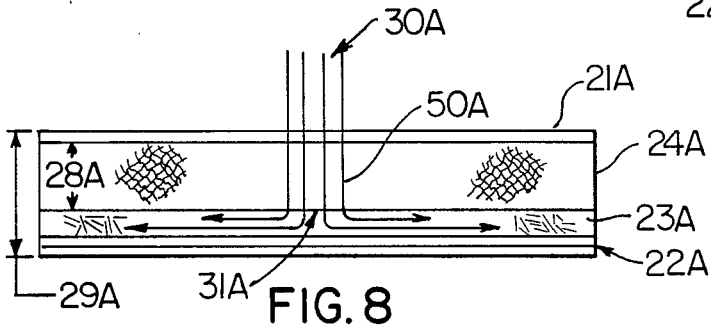
FIG. 8 is a schematic view taken essentially on the line 8—8 of FIG. 7.

The structure 24A is a resilient sheet of a foamed synthetic plastic material having a reticulated construction and such reticulated construction and foamed character thereof is illustrated typically at 25A in FIGS. 6 and 11. As best seen in FIG. 8 of the drawings, the resilient sheet or structure 24A has a predetermined thickness which is designated generally by the reference numeral 28A and the thickness 28A comprises the major portion of the overall thickness 29A of the pad assembly 20A.

The structure 24A of the pad assembly 20A is substantially the same as the structure 24 and may be made by the same process as the structure 24. The structure 24A has the same physical properties and performance characteristics as the structure 24.

The top layer 21A of the pad assembly 20A is also preferably in the form of a napped fabric tricot and as before the layer 21A may be made entirely of polyester yarns, if desired.

Figure 7:
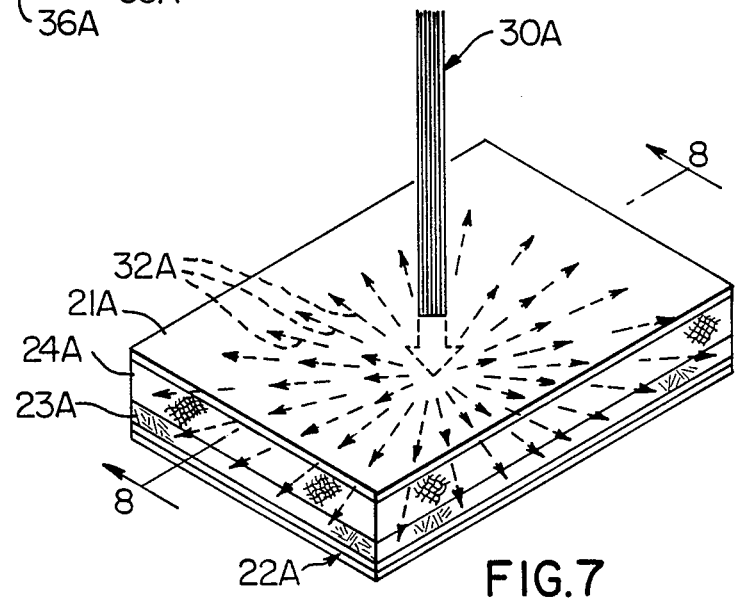
FIG. 7 is a schematic isometric view similar to FIG. 3 illustrating the manner in which the absorbent layer of the pad assembly of FIG. 1 serves to dissipate liquid radially from a local introduction point throughout a substantial volume of the absorbent layer.

The pad assembly 20A also comprises the absorbent layer 23A as mentioned earlier and as before such absorbent layer is preferably in the form of a nonwoven fibrous mat which serves to dissipate liquid radially from any local introduction point thereon throughout a substantial region or portion of its volume. This phenomenon for the pad 20A is shown in FIGS. 7 and 8 of the drawings in which liquid 30A is shown schematically by the lines 30A and is introduced at an exemplary local introduction point 31A. The construction of the fibrous mat 23A is such that such liquid is dissipated radially throughout a substantial volume of the mat 23A, as indicated by the radial dotted arrows in FIG. 7 and a representative few of such arrows are designated by the same reference numeral 32A.

The absorbent layer 23A is also preferably comprised of randomly disposed fibers as shown at 33A in FIG. 11 which are preferably in the form of randomly disposed bonded fibers 34A. The fibers 34A may be in the form of polyester or other suitable fibers.

The pad assembly 20A also comprises a waterproof layer 22A, as mentioned earlier, and such waterproof layer is best illustrated in FIGS. 6 and 11 and comprises a polymeric moisture impervious sheet portion 35A and a woven fabric portion 36A which are bonded together free of additional adhesive means therebetween.

Although the pad assembly 20A does not utilize additional adhesive means in its bottom waterproof layer between the polymeric sheet 35A and the woven fabric 36A this is not the case between the additional layers of the pad assembly as will now be described.

The pad assembly 20A comprises additional adhesive means, designated by the reference numeral 40A, disposed between its various layers and structures, and as will now be described with particular reference to FIG. 9 of the drawings. In particular, the pad assembly 20A comprises additional adhesive means 40A disposed between the top layer 21A and the multiple-purpose structure 24A, additional adhesive means 40A disposed between the structure 24A and the absorbent layer 23A, and additional adhesive means 40A between the absorbent layer 23A and the bottom waterproof layer 22A. The adhesive means or adhesive 40A has substantially no effect on the passage of liquid through the pad assembly and in particular, such adhesive has no effect on the transfer of liquid through the top layer 21A, structure 24A, and into the absorbent layer 23A where it is retained. The adhesive means or adhesive 40A may be any suitable adhesive, such as a urethane adhesive, for example.

The adhesive 40A may be applied by any suitable technique but is preferably applied using a controlled spray technique onto an associated layer. As seen in FIG. 9, the adhesive 40A in this example is sprayed against the underside of the layer 21A, is sprayed against the top surface of the water absorbent layer 23A, and is sprayed against the top surface of the waterproof layer 22A and in particular against the polymeric sheet portion 35A of such layer 22A. The amount of adhesive 40A utilized is preferably a minimum amount which is sufficient to assure lamination of the various layers yet such amount between any two layers is such that it does not effect liquid flow from the top layer 21A through the structure 24A and into the water absorbent layer 23A.

A laminated construction from which the pad assembly 20A is made may be produced in a continuous laminating process and in such a process it will be appreciated that the adhesive application or spraying technique which is utilized to apply the adhesive 40A may be done while unwinding the various layer-defining components from supply rolls thereof and then bringing such components together to define the laminated construction. Further, a laminated construction from which the pad assembly 20A is made may be produced in a batch type process whereby predetermined lengths of the layer-defining components of the same width, i.e., layers 21A, 22A, 23A, and structure 24A, are sprayed with adhesive 40A as described above and then laminated together. However, regardless of whether lamination occurs in a continuous process or in a batch process an individual pad assembly 20A is then made from the laminated construction usually by cutting the larger laminated construction down to the desired size.

However, the preferred technique for making pad assemblies 20A is to define the laminated construction, from which such pad assemblies are made, in a continuous process. Accordingly, after application of the adhesive 40A in the manner described above, a desired length of the pad assembly is wound on a supply roll thereof which is designated generally by the reference numeral 42A in FIG. 10. During this winding action the various layers 21A, 22A, and 23A and structure 24A are lightly compressed with adhesive 40A therebetween. The roll 42A thus defined is preferably maintained at normal ambient room temperature and allowed to dry and cure for a number of hours, with the preferred drying and curing time being 72 hours.

Figure 9:
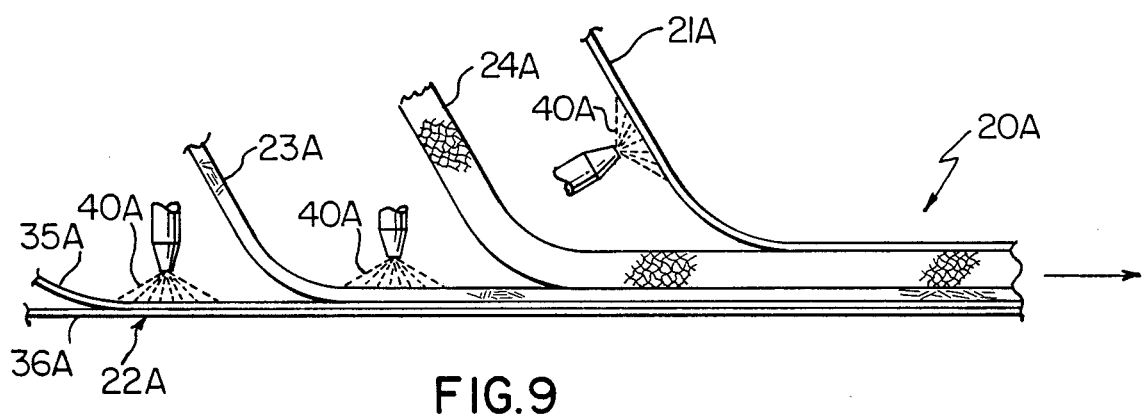
FIG. 9 is a schematic presentation particularly illustrating the manner in which adhesive means is utilized to laminate together the various components of the pad assembly of FIGS. 5-8.
Figure 10:
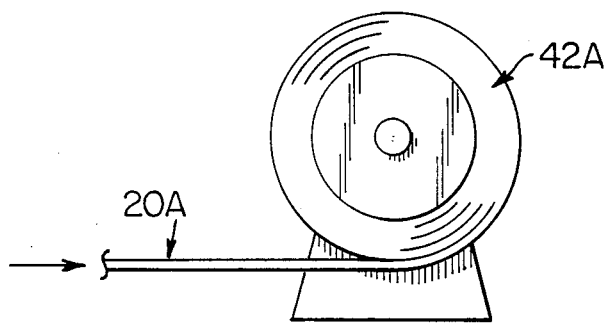
FIG. 10 is a view showing the pad assembly of FIGS. 5-8, after the application of adhesive means, rolled on a supply roll thereof to enable the weight of adjoining turns of the supply roll to serve as a means for holding the various layers or structures of the pad assembly urged together with the adhesive means disposed therebetween so that upon drying of the adhesive means the pad assembly is defined as a laminated construction.

It will also be appreciated that the spraying with the urethane adhesive 40A in the manner illustrated in FIG. 9 is preferably achieved at room temperature and the amount of adhesive spray is controlled by the operator so that a minimum amount of urethane adhesive 40A is applied which is sufficient to provide lamination of layers 21A-23A and structure 24A yet adhesive 40A is not excessive so as to prevent flow of liquid through the pad assembly.

In this example of the invention the adhesive 40A is show as being applied by spray technique; however, it will be appreciated that any other suitable technique may be utilized to apply such adhesive, as is known in the art.

The pad assembly 20A also has a binding tape which protects the peripheral edges P thereof and such binding tape is designated generally by the reference numeral 44A. As before, the binding tape 44A may be any suitable tape known in the art and may be made of any suitable material. The binding tape 44A is preferably a 100% polyester twilled or twill tape which is fastened in position by suitable stitch means or stitches 45A. In the process of stitching the binding tape 44A in position the pad assembly 20A has a compressed peripheral edge portion defined by an outer portion which has a substantially D-shaped configuration, as shown at 46A.

The pad assemblies 20 and 20A may be laundered several times a day without undue wear thereof. During laundering, each twill tape 44 and 44A respectively protects the edges of its pad assembly. Also, due to the overall construction of the pad assembly, it will be appreciated that each pad assembly 20 and 20A may be laundered several hundred times without damage thereto.

The top layer 21-21A is made of material such that the liquid 30-30A respectively passes readily therethrough. Similarly, the reticulated foam-like open structure of the structure 24-24A allows passage therethrough, as shown at 50 and 50A in FIGS. 4 and 8 respectively, with such passage being in an unobstructed manner. This enables the liquid to reach a local introduction point 31-31A, for example, on the absorbent layer 23-23A respectively and the construction of the absorbent layer is such that the liquid is dissipated radially and rapidly in the manner previously described.

Having described the construction of each pad assembly 20 and 20A and method of making same the detailed description will now proceed with typical examples of materials used for the various layers and structure of each pad assembly. For example, the top fabric layer 21-21A is a napped tricot and is readily available from a number of manufacturers. Similarly, the woven fabric 36-36A and polymeric sheet 35-35A of the waterproof layer 22-22A are also available from a number of manufacturers.

The liquid absorbent layer or mat 23-23A is available from a number of sources; and, one such source is The Medical Fabrics Company, 110 West 40th Street, New York, N.Y. 10018, and is sold under the trade designation nonwoven polyester fabric NW60. In one exemplary embodiment of this invention a 10½ ounce per square yard nonwoven water absorbent layer 23-23A was provided.

Similarly, the structure 24-24A is also available from a number of sources; and, one such source is Crest-Foam Corporation, 100 Carol Place, Moonachie, N.J. 07074, and sold under the trade designation reticulated ether foam number 40TR30WH.

It will be appreciated that the various materials selected to define the various layers of the pad assembly 20-20A and the structure 24-24A are compatible with the liquids with which such pad assembly is used. In particular, where the primary application of the pad assembly 20-20A is for the person having urinary incontinence the constituents of the pad assembly are such that urine does not cause degradation and damage to the various layers or structure of the pad assembly. The same applies where the pad assembly is particularly adapted to be used with other liquids.

The thread for the stitches or stitch means used for quilting in the pad assembly 20A and used to sew the peripheral twill tape in both pad assemblies 20 and 20A may be any suitable thread and preferably is a thread made of polyester.

In addition, the top layer 21-21A perferably has both a hydrophilic finish and an antimicrobial finish. Layer 24-24A has an antimicrobial ingredient formulated into its manufacturing foaming process. Layer 23-23A also has an antimicrobial finish. The hydrophilic finish assures rapid dissipation or spreading and absorption of liquid or moisture coming into contact with the skin of a patient laying on the pad to thereby allow rapid drying of such skin. The antimicrobial finish assures that any bacteria coming into contact with the finish will be killed upon continued contact with the finish.

Any suitable hydrophilic finish known in the art may be used; and, an exemplary finish which has been used is sold under the trade name "LR finish" by Luboch International Consultants of Charlotte, N.C.

Similarly, any suitable non-leaching antimicrobial finish may be used and an exemplary finish which has been used is sold under the trade name "SYLGARD 5700" or "SYLGARD 5701" by the Dow Corning Company of Midland, Mich. The antimicrobial finish is useful in killing a wide variety of bacteria, controls fermentation of urine, controls production of ammonia, and controls the production of odor.

The hydrophilic finish and antimicrobial finish for the top layer 21-21A are preferably liquids which may be mixed together and applied in a typical padding operation, as known in the art. In essence, the padding operation provides for moving of the top layer fabric through a bath of the mixed hydrophilic and antimicrobial liquids and squeeze rollers are used to force the mixed liquids into the fabric comprising the top layer. Layer 24-24A is spray treated with the antimicrobial finish during its manufacture.

Thus, it is seen from the above description that this invention provides a new liquid-absorbing pad assembly which provides optimum comfort to a person coming into contact therewith and such pad assembly results in a dry top layer in a very short time after such layer becomes wet. In addition, this invention provides a new method of making a liquid-absorbing pad assembly.

While the forms and methods of this invention now preferred have been illustrated and described as required by the Patent Statute it is to be understood that other forms and method steps can be utilized and still fall within the scope of the appended claims wherein each claim sets forth therein what is believed to be known in the art prior to this invention in that portion of each claim that is presented before the term "the improvement" and sets forth what is believed to be new in the art according to this invention in that portion of each claim that is presented after the term "the improvement" whereby it is believed that each claim sets forth a novel, useful and unobvious invention within the purview of the Patent Statute.

What is claimed is:

1. In a liquid-absorbing pad assembly having a peripheral outline and comprising, a top layer, a bottom waterproof layer, and an absorbent layer between said top and bottom layers, the improvement comprising, a multiple-purpose structure disposed between said absorbent layer and said top layer, said structure providing cushioning, means enabling immediate passage therethrough of liquid from said top layer, means substantially preventing reverse wicking of liquid that has passed through said structure, and a suspension which allows air to freely associate with the underside of said top layer for drying purposes,
    characterized in that
    said structure is a resilient sheet of foamed synthetic plastic material having a reticulated construction.

2. A pad assembly as set forth in claim 1 in which said top layer, structure, and absorbent layer are held together inwardly of said peripheral outline by stitch means.

3. A pad assembly as set forth in claim 2 in which said stitch means define a quilted construction.

4. A pad assembly as set forth in claim 3 in which said stitch means pull said top layer, structure, and absorbent layer together in a plurality of locations defining a patterned outline when viewed normal to said top layer, such patterned outline having a central part, and said resilient sheet has a predetermined thickness which when measured at each central part comprises a major portion of the overall thickness of said assembly.

5. A pad assembly as set forth in claim 1 in which said top layer, structure, and absorbent layer are laminated together.

6. A pad assembly as set forth in claim 5 in which said resilient sheet has a predetermined thickness which comprises a major portion of the overall thickness of said assembly.

7. A pad assembly as set forth in claim 1 in which said top layer is a top fabric layer.

8. In a liquid-absorbing pad assembly having a peripheral outline and comprising, a top fabric layer, a bottom waterproof layer, and an absorbent layer between said top and bottom layers, the improvement comprising, a multiple-purpose structure disposed between said absorbent layer and said top layer, said structure providing cushioning, means enabling immediate passage therethrough of liquid from said top layer, means substantially preventing reverse wicking of liquid that has passed through said structure, and a suspension which allows air to freely associate with the underside of said top layer for drying purposes,
    characterized in that
    said top fabric layer is a tricot.

9. A pad assembly as set forth in claim 8 in which said tricot is a napped tricot.

10. A pad assembly as set forth in claim 9 in which said napped tricot is a loop napped tricot whereby it has a napped surface texture which is defined by its knitted construction.

11. A pad assembly as set forth in claim 10 in which said napped tricot is made entirely of polyester yarns.

12. A pad assembly as set forth in claim 1 in which said absorbent layer is a nonwoven fibrous mat.

13. A pad assembly as set forth in claim 12 in which said fibrous mat serves to dissipate liquid radially from a local introduction point throughout a substantial portion of its volume.

14. A pad assembly as set forth in claim 13 in which said mat is comprised of randomly disposed bonded fibers.

15. A pad assembly as set forth in claim 14 in which said fibers comprise polyester fibers.

16. A pad assembly as set forth in claim 1 in which said waterproof layer comprises a polymeric sheet portion and a woven fabric bonded together free of additional adhesive means therebetween.

17. A pad assembly as set forth in claim 16 in which said polymeric sheet portion is made of rubber.

18. A pad assembly as set forth in claim 17 in which said woven fabric is a plainwoven fabric comprised of cotton and polyester, said woven fabric serves to protect said polymeric layer against abrasion, provides dimensional stability to said waterproof layer, and provides a non-skid surface to the bottom of said pad assembly.

19. A pad assembly as set forth in claim 18 in which said polymeric sheet portion is capable of withstanding a hydrostatic water pressure of 100 pounds per square inch gauge without allowing passage of water therethrough.

20. In a liquid-absorbing pad assembly having a peripheral outline and comprising, a top layer, a bottom waterproof layer, and an absorbent layer between said top and bottom layers, the improvement comprising, a multiple-purpose structure disposed between said absorbent layer and said top layer, said structure providing cushioning, means enabling immediate passage therethrough of liquid from said top layer, means substantially preventing reverse wicking of liquid that has passed through said structure, and a suspension which allows air to freely associate with the underside of said top layer for drying purposes,
characterized in that
adhesive means are disposed between said top layer and said multiple-purpose structure, between said multiple-purpose structure and said absorbent layer and between said absorbent layer and said bottom waterproof layer, said adhesive means having substantially no affect on the passage of liquid through said pad assembly.

21. A liquid absorbing pad adapted for use by persons suffering from incontinence, said pad being of generally rectangular outline and comprising
a bottom waterproof layer having a given outline,
an absorbent layer, having the same given outline, superposed directly on said bottom layer,
a reticulated, resilient, multi-purpose structure layer, having the same given outline, superposed directly on said absorbent layer,
a liquid permeable top layer, having the same given outline, superposed directly on said absorbent layer, and
means joining the peripheral edges of said layers,
said multi-purpose structure layer being characterized by providing
a. cushioning means for the pad,
b. means enabling immediate passage of liquid therethrough from the top layer to the absorbent layer,
c. means substantially preventing reverse wicking of liquid that has passed through the multi-purpose structure layer, and
d. a suspension for the top layer which allows air to freely associate with the underside of said top layer for drying purposes.

22. A pad set forth in claim 21 in which the multiple-purpose structure layer comprises foamed, synthetic plastic material.

23. A pad as set forth in claim 22 in which the absorbent layer comprises a non-woven fibrous mat.

24. A pad as set forth in claim 23 in which
each of said layers has a substantially uniform thickness,
the thickness of the multi-purpose structure layer comprises a major portion of the combined thickness of said layers.

25. A pad as set forth in claim 21 in which
a plurality of laterally spaced means secure in the top layer and absorbent layers together and compress the resilient, multipurpose layer therebetween.

26. A pad as set forth in claim 21 in which the laterally spaced means comprise stitching disposed in quilted fashion.

27. A pad as set forth in claim 21 in which
said layers and the means joining the peripheral edges thereof are washable,
whereby the incontinent pad is capable of repeated reuse.

28. In a method of making a liquid-absorbing pad assembly which has a peripheral outline, said method comprising the steps of, providing a top layer, providing a bottom waterproof layer, and disposing an absorbent layer between said top and bottom layers, the improvement comprising the steps of, providing a multiple-purpose structure, disposing said structure between said absorbent layer and said top layer, said structure providing cushioning, means enabling immediate passage therethrough of liquid from said top layer, means substantially preventing reverse wicking of liquid that has passed through said structure, and a suspension which allows air to freely associate with the underside of said top layer for drying purposes,
characterized in that
the step of providing said structure comprises
providing said structure as a resilient sheet of foamed synthetic plastic material having a reticulated construction.

29. In a method of making a liquid-absorbing pad assembly which has a peripheral outline, said method comprising the steps of, providing a top layer, providing a bottom waterproof layer, and laminating an absorbent layer between said top and bottom layers, the improvement comprising the steps of, providing a multiple-purpose structure, and laminating said multiple-purpose structure between said absorbent layer and said top layer and inwardly of said peripheral outline employing adhesive means, said structure providing cushioning, means enabling immediate passage therethrough of liquid from said top layer, means preventing reverse wicking of liquid that has passed through said structure, and a suspension which allows air to freely associate with the underside of said top layer for drying purposes, said adhesive means having substantially no effect on the passage of liquid through said pad assembly.

30. A method of making a pad assembly as set forth in claim 28 and comprising
the further step of stitching said top layer, said structure and absorbent layer together inwardly of said peripheral outline with stitch means.

31. A method of making a pad assembly as set forth in claim 30 in which said stitching step defines said top layer, said structure and absorbent layer as a quilted construction inwardly of said peripheral outline.

32. A method of making a pad assembly as set forth in claim 29 in which
said step of laminating said multiple-purpose structure between said absorbent layer and said top layer employing additional adhesive means comprises
disposing adhesive means between said top layer and said multiple-purpose structure and between said multiple-purpose structure and said absorbent layer and
comprising the further step of
employing adhesive means between said absorbent layer and said bottom waterproof layer.

33. A pad assembly as set forth in claim 32 in which said adhesive means comprises a urethane adhesive.

34. A pad assembly as set forth in claim 33 in which said urethane adhesive is applied by a controlled spray technique to an associated layer.

* * * * *